US012661281B2

(12) United States Patent
Simmonds et al.

(10) Patent No.: US 12,661,281 B2
(45) Date of Patent: Jun. 23, 2026

(54) INDIVIDUALLY PACKAGED ABSORBENT ARTICLE

(71) Applicant: Pixie, Inc., New York, NY (US)

(72) Inventors: Fiona Simmonds, New York, NY (US); Sana Clegg, New York, NY (US)

(73) Assignee: Pixie, Inc., New York, NY (US)

( * ) Notice: Subject to any disclaimer, the term of this patent is extended or adjusted under 35 U.S.C. 154(b) by 314 days.

(21) Appl. No.: 18/569,049

(22) PCT Filed: Jun. 22, 2022

(86) PCT No.: PCT/US2022/034545
§ 371 (c)(1),
(2) Date: Dec. 11, 2023

(87) PCT Pub. No.: WO2023/278213
PCT Pub. Date: Jun. 5, 2023

(65) Prior Publication Data
US 2024/0269015 A1 Aug. 15, 2024

Related U.S. Application Data

(60) Provisional application No. 63/216,813, filed on Jun. 30, 2021.

(51) Int. Cl.
*A61F 13/551* (2006.01)
(52) U.S. Cl.
CPC ...... *A61F 13/5514* (2013.01); *A61F 13/5515* (2013.01)

(58) Field of Classification Search
CPC .......................... A61F 13/5514; A61F 13/5515
See application file for complete search history.

(56) References Cited

U.S. PATENT DOCUMENTS

| | | | | |
|---|---|---|---|---|
| 4,648,513 | A | * | 3/1987 | Newman ................. B65B 9/067 383/902 |
| H1363 | H | * | 10/1994 | Leeker ................. A61F 13/5514 206/440 |
| 5,884,771 | A | | 3/1999 | McCormick |
| 6,716,203 | B2 | | 4/2004 | Sorebo et al. |
| 8,900,210 | B2 | | 12/2014 | Drevik |
| 11,013,644 | B2 | | 5/2021 | Roszkowiak et al. |

(Continued)

FOREIGN PATENT DOCUMENTS

| | | | | |
|---|---|---|---|---|
| DE | 4133095 A1 | * | 10/1992 | ............. B65D 33/28 |
| JP | 2018020833 A | * | 2/2018 | |

OTHER PUBLICATIONS

International Preliminary Report on Patentability issued Dec. 14, 2023 in International (PCT) Application No. PCT/US2022/034545.

(Continued)

*Primary Examiner* — Rebecca E Eisenberg
*Assistant Examiner* — Matthew Wrubleski
(74) *Attorney, Agent, or Firm* — Wenderoth, Lind & Ponack, L.L.P.

(57) ABSTRACT

An individually packaged absorbent article, comprising a wrapper material configured into a bag and comprising a drawstring, and a single absorbent article removably positioned within the wrapper material; a hygiene kit comprising the individually packaged absorbent article; and a method of discarding an absorbent article.

16 Claims, 3 Drawing Sheets

(56) References Cited

U.S. PATENT DOCUMENTS

| | | |
|---|---|---|
| 2006/0135926 A1 | 6/2006 | Dick et al. |
| 2007/0045144 A1 | 3/2007 | Wheeler et al. |
| 2011/0028933 A1* | 2/2011 | Fung ..................... B65B 69/00 |
| | | 604/385.02 |
| 2013/0110062 A1* | 5/2013 | Glenn ................ A61F 13/5515 |
| | | 604/359 |
| 2018/0022483 A1* | 1/2018 | Lenon, III ............. B65F 1/002 |
| | | 53/469 |
| 2018/0369030 A1 | 12/2018 | Myles |
| 2019/0350776 A1* | 11/2019 | Roszkowiak ....... A61F 13/5512 |

OTHER PUBLICATIONS

International Search Report and the Written Opinion of the International Searching Authority dated Oct. 6, 2022 in International (PCT) Application No. PCT/US2022/034545.
Aniket Bhute et al., "Overview of Nonwovens Bonding Technologies," Textile Value Chain, vol. 3, Issue. 6, pp. 26-28, Jun. 11, 2015.
Extended European Search Report dated Apr. 23, 2025 in European Patent Application No. 22833927.1.

* cited by examiner

INDIVIDUALLY PACKAGED ABSORBENT ARTICLE

CROSS-REFERENCE TO RELATED APPLICATIONS

This application claims priority to U.S. Provisional Application No. 63/216,813 filed Jun. 30, 2021, which is incorporated by reference herein in its entirety.

BACKGROUND OF THE INVENTION

The present invention relates to an individually packaged absorbent article, such as, a feminine sanitary pad or napkin. More specifically, the present invention relates to an improved packaging of an absorbent article.

Absorbent feminine care articles, such as panty liners, sanitary pads, and maxi pads and other absorbent care products not specifically related to feminine care, such as incontinence pads, which are used by both males and females, are used to absorb various bodily fluids, such as, menses, urine and other bodily fluids. The majority of these absorbent articles are used on a recurring basis to absorb vaginal discharge throughout the month, and, during a woman's menstrual cycle, discharged blood and other fluid and particles.

Absorbent articles are primarily sold in two configurations, either in packaging that contains individually wrapped sanitary products or in packaging where the products are not individually wrapped but rather stacked on top of each other. The individually wrapped products are carried by a consumer for use when outside of the home. Individually wrapping each product protects the interior of the absorbent product (i.e., the sanitary part that is worn against and touches the skin) from contaminants which may be present in a bag, purse, pocket or container in which it is carried.

Conventionally, a product wrapper includes at least one thermoplastic film or sheet material, such as polyethylene, which is folded around the absorbent article and sealed by using heat and/or pressure, ultrasonics, or an adhesive to form a packaged article. The package is designed to be opened by breaking or tearing the material to reveal the absorbent product within the wrapper.

Most females prefer privacy when carrying or using feminine care products. In particular, young girls are especially sensitive to ensuring privacy when using a restroom both in or out of the home. The teenage years are filled with numerous physical changes that occur at different times for each girl. The preteen and teenage years are filled with a desire to "fit in" instead of "standing out" and being teased. During these years, some girls have started menstruating while others have not. Using a bathroom of any type during this period can be an anxiety inducing and stressful experience. There are two main reasons for this anxiety.

The primary reason for this anxiety is the distinctive noise of traditional wrappers for absorbent products. For instance, using an absorbent product in a school bathroom within earshot of peers or at a friend's house within earshot of siblings and family members signals to listeners that the user is currently menstruating, and, in turn, can be a mortifying experience for the girl.

Existing wrappers are loud. They crinkle and crack when handled. They also have heat sealed edges that, when ripped or torn open to expose the absorbent within, create a loud noise.

U.S. Pat. No. 6,716,203 attempts to improve on the noise problem by using a quieter wrapper material to create quieter seams. However, the noise is not eliminated, because the user is still required to tear the sealed wrapper material away from absorbent article or use their finger to tear a seal in the wrapper material to expose the absorbent article. Thus, the user's ability to discreetly open the packaging to reveal the absorbent article is hampered by the need to tear or rip open sealed packaging to obtain and use the absorbent article.

The secondary reason for the above-described anxiety is the nature of disposal of a sanitary product. Absorbent articles are not designed to be flushed down the toilet, because this can cause plumbing and other environmental problems. When an absorbent article is to be discarded, conventional packages are designed so that a used article can be rolled up in the wrapper for disposal. However, this conventional disposal method allows for the used product to easily become unrolled and/or for any blood or fluids that have been absorbed on the edges of the article to be visible from a trash receptacle. Alternatively, when an article wrapper is not used, conventionally the user will wrap the used article in toilet paper in the same manner for disposal. Thus, the consumer's ability to dispose of the absorbent article discreetly is limited by the design of the packaging materials. There is no effective alternative.

U.S. Patent Application Publication No. 2013/0110062 discloses a feminine health pouch for storing a used absorbent article. However, this pouch as carried does not hold the clean unused absorbent articles, such as a menstrual pad. Rather, this pouch is unattached and carried separately from clean pads. It is used as a discrete bag to hold used absorbent articles, such as menstrual pads and tampons for disposal.

The present inventors have created an individually packaged absorbent article that can be quietly opened without tearing the packaging or breaking any seal. The individually packaged absorbent article holds a clean unused absorbent article, which can be easily replaced with a used absorbent article to discretely discard the used absorbent article without worrying about the used article unraveling from the wrapper or becoming visible in a trash receptacle. As a result of the invention, the two common anxieties accompanying menstruation, especially in younger consumers, can be reduced or avoided altogether.

BRIEF SUMMARY OF THE INVENTION

The invention is illustrated as follows:

[1] An individually packaged absorbent article, comprising:

a wrapper material configured into a bag and comprising a drawstring, and a single absorbent article removably positioned within the wrapper material.

[2] The individually packaged absorbent article according to [1], wherein the wrapper material comprises a channel and the drawstring is threaded through the channel in a loop.

[3] The individually packaged absorbent article according to [2], wherein the channel is on an inside or an outside of the bag configuration.

[4] The individually packaged absorbent article according to [3], wherein the channel is on the outside of the bag configuration.

[5] The individually packaged absorbent article according to [2], wherein the wrapper material further comprises a first cut out at a loop side of the channel and a second cut out at a string ends side of the channel.

[6] The individually packaged absorbent article according to [1], wherein the drawstring comprises two string ends having a length accessible by a user.

[7] The individually packaged absorbent article according to [1], wherein the single absorbent article is positioned within the wrapper material in a bi-fold or a tri-fold.

[8] The individually packaged absorbent article according to [1], wherein the single absorbent article comprises a nonskin-touching outer surface folded over a skin-touching inner surface, and a portion of the folded nonskin-touching outer surface faces an opening of the wrapper material of the bag configuration.

[9] The individually packaged absorbent article according to [1], wherein the single absorbent article absorbs at least one fluid selected from the group consisting of menstrual fluid, vagina discharge, urine, blood, and another bodily fluid.

[10] The individually packaged absorbent article according to [1], wherein the single absorbent article is a sanitary napkin.

[11] The individually packaged absorbent article according to [10], wherein the sanitary napkin is at least one selected from the group consisting of a menstrual pad, a liner, an incontinence pad, a medical pad, and an overnight pad.

[12] The individually packaged absorbent article according to [1], wherein the wrapper material is configured into an open bag configuration.

[13] The individually packaged absorbent article according to [1], wherein the wrapper material is configured into a closed bag configuration.

[14] The individually packaged absorbent article according to [1], wherein the wrapper material is at least one material selected from the group consisting of a nonwoven material, a plastic material, a plant-based material, a nonporous material, a porous material, an absorbent material, and a waterproof material.

[15] The individually packaged absorbent article according to [1], wherein the wrapper material is a nonwoven material.

[16] The individually packaged absorbent article according to [1], wherein the wrapper material further comprises a decorative layer.

[17] The individually packaged absorbent article according to [1], which is a single-use article.

[18] A hygiene kit comprising the individually packaged absorbent article according to [1].

[19] A method of discarding an absorbent article, comprising:

removing a first single absorbent article from the individually packaged absorbent article according to [1] to obtain an empty wrapper material, placing a second single absorbent article into the empty wrapper material to obtain a used product, tightening the drawstring, and discarding the used product.

[20] The method according to [19], further comprising rolling, folding or otherwise condensing the second single absorbent article, and knotting the drawstring.

[21] The method according to [20], further comprising winding the drawstring around the used product.

DETAILED DESCRIPTION OF THE INVENTION

The present invention relates to a wrapper material configured into a bag and having a drawstring to removably hold an individual absorbent article, such as, a menstrual pad, a liner, an incontinence pad, a medical pad, an overnight pad, and the like, which can be used and then disposed in the wrapper material. Thus, for example, the individual absorbent article is first stored in the wrapper material, then removed for use and replaced with a second absorbent article, and then the bag is closed and the package is thrown away.

The wrapper material is configured into a bag. In this description, "the wrapper material configured into a bag" may also be referred to as "the wrapper material bag" or "the bag".

Figure 1:
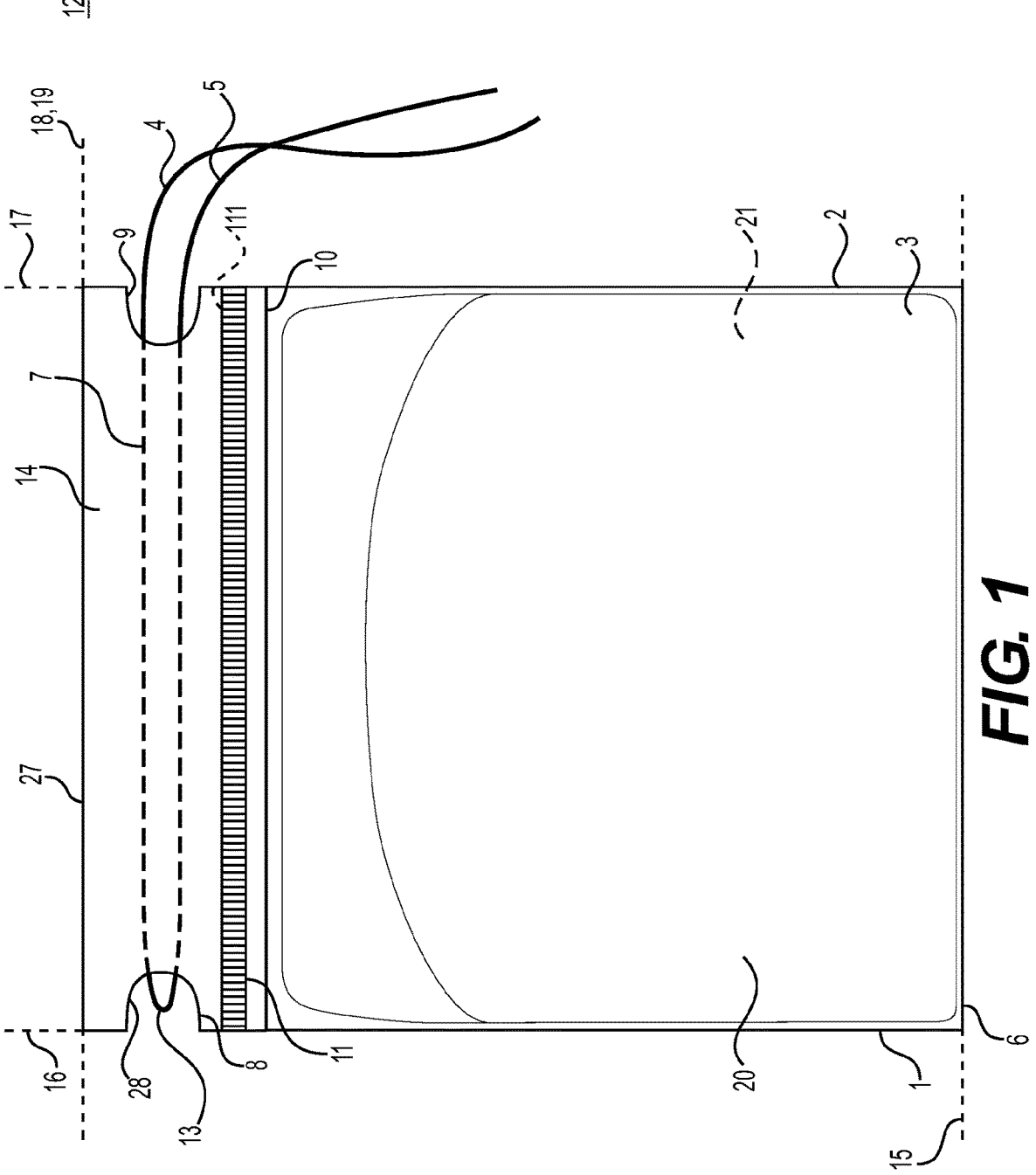
FIG. 1 is a front view of an individually packaged absorbent article according to the invention.

FIG. 1 depicts an individually packaged absorbent article 12. The wrapper material bag is created by folding a single piece of wrapper material back onto itself in equal lengths along a bottom axis 15. The bottom axis 15 creates a bag bottom 6. The folding also creates a front wrapper material 20 and a back wrapper material 21 having a first perpendicular axis 16 and a second perpendicular axis 17 perpendicular to the bottom axis 15. The front wrapper material 20 and the back wrapper material 21 are bonded together at the first perpendicular axis 16 and the second perpendicular axis 17 to create a wrapper material bag 14 having a bag configuration having a closed bottom 6, closed sides at first and second material edges 1,2 and a bag top 27. The bonding creates a bond or seal strong enough to hold the first and second material edges 1,2 together so that the front wrapper material 20 does not separate or tear away from the back wrapper material 21 when under pressure from removing or inserting an absorbent article 3.

Opposite to the bottom axis 15, the front wrapper material 20 is folded along a top front axis 18 towards the bottom axis 15 and a front bond 11 on the front wrapper material 20 is made. Opposite to the bottom axis 15, the back wrapper material 21 is folded along a top back axis 19 towards the bottom axis 15 and a back bond 111 on the back wrapper material 21 is made. The folds of the front and back wrapper material 20, 21 along the top front and back axes 18, 19 can be on the outside of the bag configuration or on the inside of the bag configuration. The folds and bonds 11, 111 create a channel 28 along the entire perimeter of the top of the bag (bag top 27) for a drawstring 7.

The drawstring 7 has a loop 13 on one side of the bag, such as at the first perpendicular axis 16 side of the bag, and two string ends 4, 5 on the side opposite to the loop 13, such as at the second perpendicular axis 17 side of the bag. The drawstring 7 can be any length so long as it loops through the entire channel 28 and exits the channel. In embodiments, the string ends 4,5 are long enough to be accessible to a user to pull the drawstring and close the top of the bag 27. In preferred embodiments, the drawstring 7 is long enough for a user to tie a knot with the string ends 4,5 when the wrapper material bag 14 is closed. In embodiments, the drawstring 7 is long enough for a user to close the bag and wind the drawstring 7 around the bottom 6 and top 27 of the bag 14.

The drawstring 7 enables a user to use the bag to discretely dispose of the absorbent article by placing a soiled or used absorbent article within the bag, and use the drawstring to close and knot the bag to completely conceal the used absorbent article.

The channel 28 may have exposed cut out sections. For example, in embodiments, a first cut out 8 can be at the loop 13 side and a second cut out 9 can be at the string ends 4,5 side of the wrapper material bag 14. The first and second cut outs 8,9 can permit the loop 13 and string ends 4,5 to create a narrow inner cylinder near the bag top 27 and keep the removable absorbent article 3 secured in the wrapper material bag 14. However, the absorbent article 3 is secured in the wrapper bag 14 by friction between the absorbent article 3 and the wrapper material. As a result, exposed cut out sections are optional and not required. Additional exposed cut sections besides the first and second cut outs 8,9 are also possible.

In the individually wrapped absorbent article 12, an absorbent article 3 is removably positioned in the wrapper material bag 14. In preferred embodiments, the size of the absorbent article 3 and the size of the wrapper material bag 14 are coordinated so that the absorbent article 3 uses most of the volume of the wrapper material bag 14 and fits snuggly within the wrapper material bag 14. Friction between the inside of the wrapper material bag 14 and the absorbent article 3 keeps the absorbent article 3 positioned within the wrapper material bag 14, even when the bag top 27 is open and the bag is turned upside down. The absorbent article 3 can be folded within the wrapper material bag 14, such as in a bi-fold or a tri-fold. The absorbent article 3 can have any number of folds, so long as a folded absorbent article fits snuggly within the wrapper material bag 14.

Figure 2:
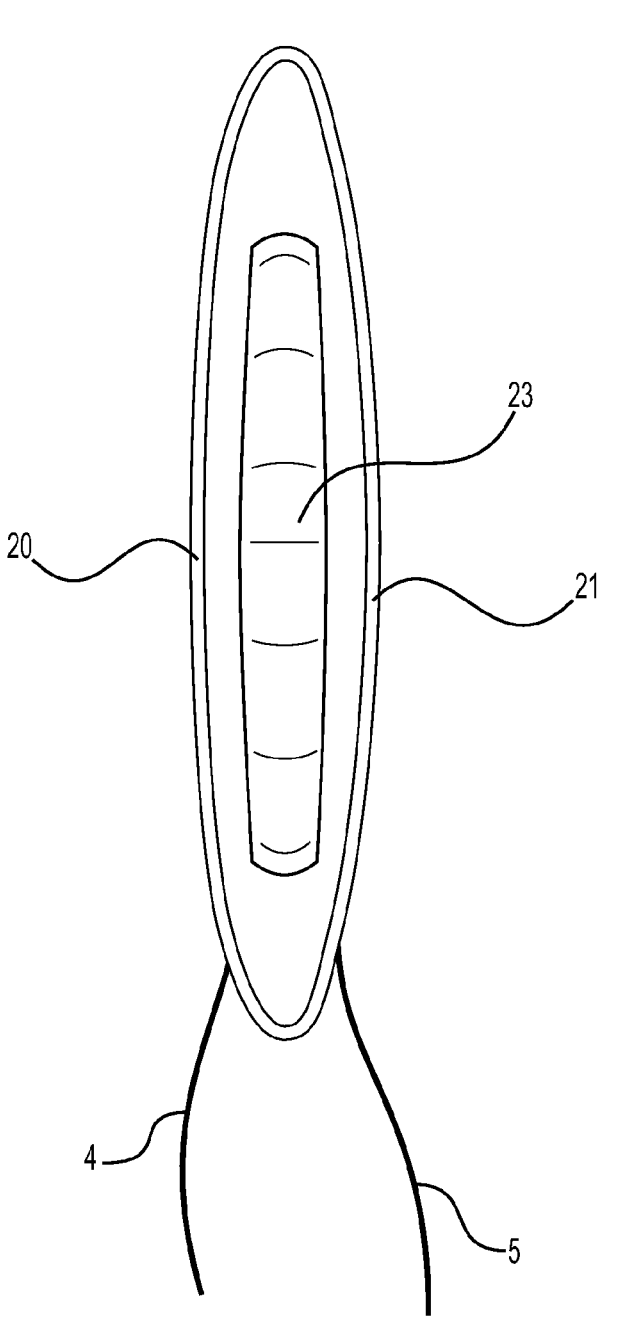
FIG. 2 is a top end view of the individually packaged absorbent article according to the invention.

FIG. 2 is a top end view of the individually packaged absorbent article 12 shown in FIG. 1 in which the wrapper material bag 14 is open. In FIG. 2, a nonskin-touching outer surface 23 of the absorbent article 3 is folded over a skin-touching inner surface (not shown) to keep the skin-touching inner surface sanitary. A portion of the folded nonskin-touching outer surface 23 faces an opening of the bag top 27. The front wrapper material 20 and back wrapper material 21 create friction with the absorbent article 3 to keep the absorbent article 3 positioned within the wrapper material bag 14, even when the bag is turned upside down.

In addition, as shown in FIG. 1, the first and second cut outs 8,9, can reduce the circumference of the loop 13 thereby creating a smaller circumference of the wrapper material bag 14 compared to the circumference of the top of the bag 27. The circumference of the loop 13 can be reduced by pulling the string ends 4,5. By making the loop 13 smaller, the absorbent article 3 can be even more securely held inside the wrapper material bag 14, even when the bag is turned upside down.

Figure 3:
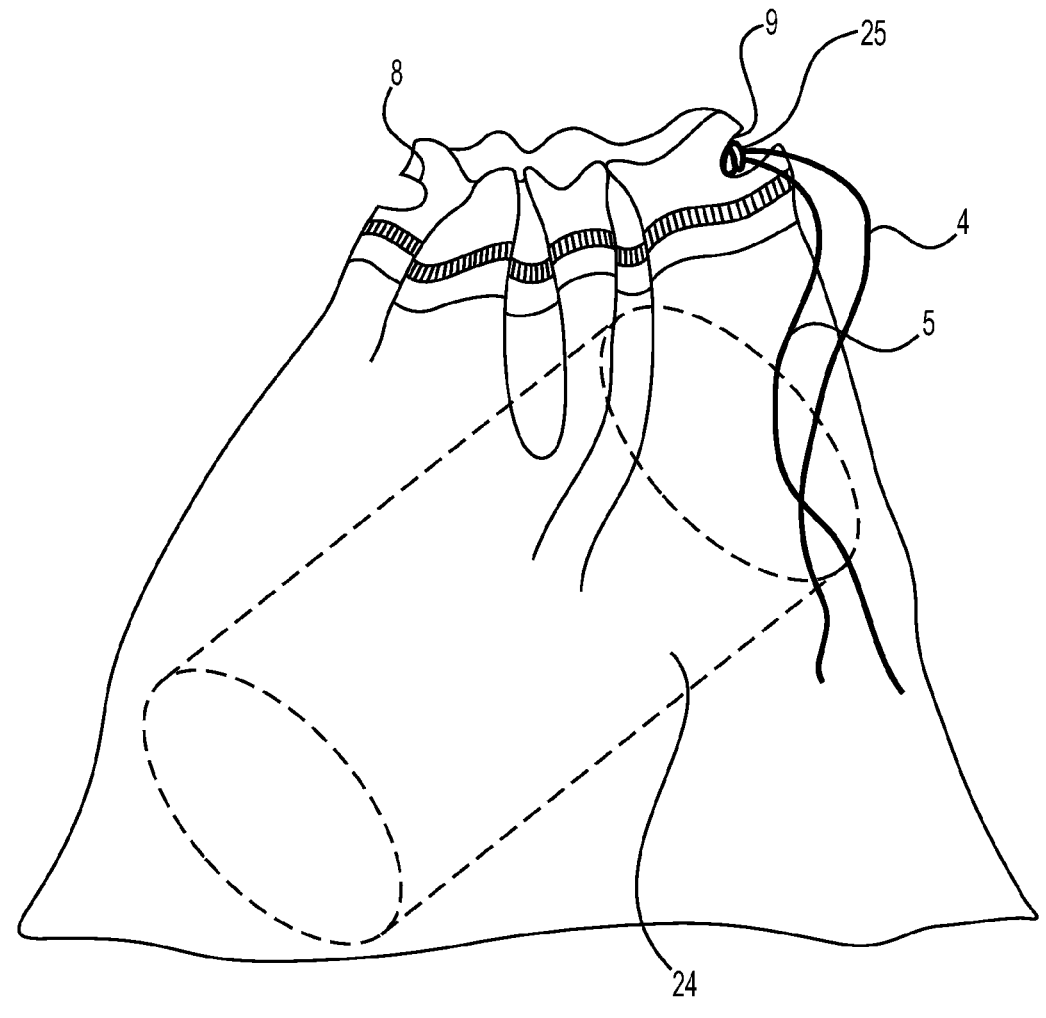
FIG. 3 depicts a used product ready for disposal. The absorbent article has been removed from the individually packaged absorbent article and replaced with a used absorbent article, and the used product is ready for disposal.

FIG. 3 depicts a used product 26. In FIG. 3, the absorbent article 3 has been removed from the individually packaged absorbent article 12 of FIG. 1, and replaced with a used absorbent article 24. The used absorbent article 24 is rolled or folded in some manner and placed back into the wrapper material bag 14. Adhesive(s) on the used absorbent article 24 may stick to the inside of the wrapper material bag 14, further securing the used absorbent article 24 in the wrapper material bag 14. The wrapper material bag 14 is closed by pulling the string ends 4,5 and may be tied with a knot 25 in the drawstring 7. The knot 25 secures the used absorbent article 24 in the wrapper material bag 14, although tying a knot is not required. The user can then discreetly discard the used product 26.

Wrapper Material

The wrapper material can be made with any suitable material in the art. For example the wrapper material can be a nonwoven material, a plastic material, a plant-based material, a nonporous material, a porous material, an absorbent material, a waterproof material, or combinations thereof.

In preferred embodiments, the wrapper material is a nonwoven fabric. A nonwoven material is fabric-like in nature and feel, but made from short and long fibers bonded together by chemical, mechanical, heat or solvent treatment. The term is used in the textile industry to denote fabrics which are neither woven or knitted.

Nonwoven materials are known in the art as sheet or web structures bonded together by entangling fiber or filaments (and by perforating films) mechanically, thermally, or chemically. They are flat, porous sheets that are made directly from separate fibers or from molten plastic or plastic film. They are not made by weaving or knitting and do not require converting the fibers to yarn.

In various embodiments, synthetic fibers of the nonwoven material may be made of, for example, polyesters, including polyethylene terephthalate (PET), polytrimethylene terephthalate (PTT), polybutylene terephthalate (PBT), and polylactic acid (PLA), and alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers), polystyrenes, polyamides, polyhydroxyalkanoates (PHA) and e.g., polyhydroxybutyrate (PHB), and starch-based compositions including thermoplastic starch, for example. The constituents of the fibers may be derived from biological sources such as plant matter, such as for PLA or biopolyethylene (bio-PE), for example. The above polymers may be used as homopolymers, copolymers, blends, and alloys thereof. In the various embodiments, natural fibers of the nonwoven structures may be made of, but not limited to, digested cellulose fibers from softwood (derived from coniferous trees), hardwood (derived from deciduous trees) or cotton, including rayons and cotton, fibers from Esparto grass, bagasse, kemp, flax, jute, kenaf, sisal, and other lignaceous and cellulose fiber sources. The fibers may comprise other constituents for color, strength, aging stability, odor control or other purposes.

For example, the nonwoven material may be any of the nonwoven materials disclosed in U.S. Pat. Nos. 10,993,855; 11,000,429; 10,968,552; and 10,857,043, each of which is incorporated by reference in its entirety. In embodiments, the wrapper material is a dispersible material, such as the dispersible wipe material disclosed in U.S. Pat. No. 10,973,384, which is incorporated by reference in its entirety.

The wrapper material can be any color, including white. The wrapper material can include one or more additional layers on the inside or outside of the wrapper bag. For example, one or more decorative layers can be on the outside of the wrapper bag. The wrapper material can also include one or more additional layers on the inside or outside of the wrapper material bag, such as one or more odor-reducing layers, water-proof layers, absorbent layers, porous layers and nonporous layer.

In embodiments, the one or more additional layers further conceal a used absorbent article within the wrapper material bag, which is ready for disposal. For example, vertical colored stripes can be printed on the wrapper material to conceal the absorbent article. In preferred embodiments, the vertical stripes are yellow, navy or magenta. In more preferred embodiments, darker colors, such as navy and magenta, are used with larger wrapper material bags, which contain larger absorbent articles that can hold a heavier menstrual flow. Any pattern, color, shape or design may be applied to the wrapper material bag.

Drawstring

The drawstring can be any general string made out of standard textile fibers, such as cotton twine, yarn, braided nylon, polypropylene twine, acrylic twine, flax twine, hemp twine, jute twine, sisal parcel string, wool, henequen, and silk. In preferred embodiments, natural twine, such as hemp, cotton, flax, silk or sisal are used. In more preferred embodiments, cotton or flax twine is used.

The drawstring can be any color, including white. The drawstring may include additional fibers to enhance the appearance or smell of the individually packaged absorbent article. The drawstring may also include odor-reducing fibers or colored fibers.

The drawstring can be any length suitable to extend throughout the channel and be accessible by a user. For example, the drawstring is about 10 to 26 cm, preferably about 12 to 24 cm, more preferably about 14 to 22 cm, even more preferably about 16 to 20 cm, and most preferably about 17 to 19 cm. In preferred embodiments, the drawstring is about 18 cm. The length of the drawstring can be adjusted depending on the size of the channel and wrapper material bag.

Absorbent Article

An "Absorbent article" refers to a device that absorbs body fluid, such as menstrual fluid, vagina discharge, urine, blood, and any other bodily fluid.

The absorbent article is a single-use disposable article, which is not intended to be laundered or reused. The term "single-use" is intended to mean that it is used one time as an absorption device, and then discarded preferably using the wrapper material bag, although the absorbent article can be discarded without using the wrapper material bag.

The absorbent article can be any commercially available absorbent article, such as a menstrual pad, a liner, an incontinence pad, a medical pad, and an overnight pad.

For example, the menstrual pad can be any Always® brand product, such as Infinity Pads with Flexfoam, Pure Cotton Pads with Flexfoam, Radiant Pads, Ultra Thin Pads, Maxi Pads, Overnight Pads, Pure Pads and Special Pads for Teens. In embodiments, the menstrual pad is, for example, an Always® Radiant Teen Pad. Alternatively, the menstrual pad can be any other commercially available absorbent article, such as a Stayfree® brand product, for example, a Stayfree® Maxi Super Pad and Stayfree Ultra Thin Regular Pad, or any Kotex® brand product, such as U by Kotex® Extra Absorbency Ultra Thin Teen Pads with Wings, and the like.

The absorbent article can also be any commercially available liner, such as any Always®, Stayfree® and Kotex® branded line.

The absorbent article may also be any commercially available incontinence pad, medical pad, and/or an overnight pad.

In embodiments, the absorbent article includes adhesive(s), which can be used to adhere the absorbent article to a user's underwear or panties.

In embodiments, the absorbent article may also include adhesive(s), which can be used to adhere the absorbent article to itself and maintain a closed position prior to use.

For example, the absorbent articles disclosed in any of U.S. Pat. Nos. 10,675,195; 10,322,032; 8,969,652; 8,502,013; 10,022,468; and 9,993,374 may be used. Each one of these U.S. patents is incorporated by reference in its entirety.

The absorbent article can be any size so long as it can be removably positioned within the wrapper material bag.

For example, an unfolded absorbent article can have a length of about 150 to 300 mm, about 180 to 250 mm, about 185 to 245 mm or about 190 to 240 mm. In preferred embodiments, the unfolded length is about 185 to 195 mm, more preferably about 187 to 193 mm, and more preferably about 189 to 191 mm, and most preferably about 190 mm. In embodiments, the unfolded length can be about 205 to 215 mm, more preferably about 207 to 213 mm, and more preferably about 209 to 211 mm, and most preferably about 210 mm. In embodiments, the unfolded length is about 235 to 245 mm, preferably about 237 to 243 mm, more preferably about 239 to 241 mm, and most preferably about 240 mm.

When folded, such as in a trifold or a bifold, the width of the absorbent article is about 50 to 100 mm, preferably about 60 to 95 mm, more preferably about 65 to 90 mm, even more preferably about 65 to 75 mm, and most preferably about 68 to 72 mm, such as about 69, 70 or 71 mm. In embodiments, the width of the folded absorbent article is about 65 to 75 mm, preferably about 67 to 73 mm, more preferably 69 to 71 mm, most preferably about 70 mm. In embodiments, the width of the folded absorbent article is about 80 to 95 mm, preferably about 82 to 93 mm, more preferably about 85 to 90 mm, even more preferably about 86 to 89 mm, and most preferably about 87 or 88 mm.

The thickness of the absorbent article when unfolded is about 1 to 10 mm, preferably about 3 to 7 mm, more preferably about 4 to 6 mm, such as about 4, 5 or 6 mm. When folded, the thickness of the absorbent article is about 2 to 30 mm, preferably about 3 to 10 mm, more preferably about 5 to 10 mm, and most preferably about 6 to 8 mm, such as about 6, 7 or 8 mm.

In preferred embodiments, the absorbent article has an unfolded length of about 190 mm, a folded length of about 85 mm, a folded width of about 70 mm and a folded thickness of about 6 mm.

In preferred embodiments, the absorbent article has an unfolded length of about 210 mm, a folded length of about 86 mm, an unfolded width of about 69 mm, a folded width of about 87 mm, an unfolded thickness of about 4 mm, and a folded thickness of about 7 mm.

In preferred embodiments, the absorbent article has an unfolded length of about 240 mm, a folded length of about 100 mm, an unfolded width of about 74 mm, a folded width of about 87 mm, an unfolded thickness of about 5 mm, and a folded thickness of about 8 mm.

Bonding

Any bonding in the wrapper material can be created by any known bonding process suitable for a wrapper material. For example, when the wrapper material is a nonwoven material, the bonding may be any type of web bonding, such as needle punching, hydro-entangling, thermal bonding, stitch bonding, or chemical bonding. These types of bonding techniques are described, for example, in Aniket Bhute et al., "Overview of Nonwovens Bonding Technologies," Textile Value Chain, Vol. 3, Issue. 6, pp. 26-28, Jun. 11, 2015, the entirety of which is incorporated by reference herein. In preferred embodiments, the bonding is thermal bonding or chemical bonding, more preferably thermal bonding. In embodiments, the thermal bonding is calendar bonding.

In other embodiments, the bonding is created with an adhesive applied to the wrapper material. Any adhesive suitable for bonding or sealing a wrapper material may be used. For example, a water-based adhesive, comprising a natural or synthetic adhesive polymer component and an aqueous component may be used. The natural polymer can be made from sources such as (i) proteins and protein-based compounds such as casein, soya proteins, zein, and gelatin, (ii) gums and gum-like materials such as gum arabic, gum tragacanth, gum ghatti, Indian gum, mucilage and the like, (iii) polysaccharide-based materials such as starch and processed starch, dextrins, agar, pectin, and the like or (iv) glues derived from animal products such as hides, bones, and fish offal. The synthetic polymers can be selected from PEI (polyethyleneimine), PAE (polyamidoamin-epichlorhydrine) and PVAm (polyvinylamine), polyvinyl alcohol (PVA), polyvinyl acetate (PVAC), vinyl acetate-ethylene (VAE), polyvinylpyrrolidone (PVP), sodium polyacrylate, polyethylacrylate, polymethacrylic acid, polyurethanes and styrene-butadiene, and water-soluble or -dispersible cellulose-based compounds such as carboxymethyl cellulose, sodium carboxymethyl cellulose, methyl cellulose, and ethyl cellulose, or any combination thereof.

The adhesive should be non-toxic and it should be approved to be used in connection with personal hygiene products.

In preferred embodiments, the bonding is thermal bonding or chemical bonding, more preferably thermal bonding, such as calendar bonding, without an adhesive.

Hygiene Kit

In another embodiment of the invention, the individually packaged absorbent article is part of a hygiene kit. The hygiene kit, for example, includes the individually packaged absorbent article and at least one other hygiene product, such as a tampon, facial tissue, another absorbent article (such as a menstrual pad, a liner, an incontinence pad, a medical pad, or an overnight pad), a toothbrush, toothpaste, dental floss, a non-steroidal anti-inflammatory drug (NSAID), a cotton swab, a razor, shaving cream or gel, a comb, a hairbrush, a shower cap, deodorant, antiperspirant, shampoo, conditioner, soap, a facial mask, hand lotion, body lotion, sunscreen, and the like.

Method of Discarding an Absorbent Article

Another embodiment of the invention is a method of discarding an absorbent article. The method comprises removing the absorbent article from the individually packaged absorbent article to empty the wrapper material bag, then replacing it with a used absorbent article to obtain a used product. Then, the used product is discarded.

In embodiments, the method further comprises winding the drawstring around the used product to further conceal the used absorbent article and the used product.

In embodiments, the method further comprises first rolling, folding, or otherwise condensing the used absorbent article, thereby reducing its size and conspicuousness, and then placing the used absorbent article into the wrapper material bag for disposal.

In embodiments, adhesive(s) on the used absorbent article adhere(s) the used article to the inside of the wrapper material bag to further conceal the used article and further reduce the conspicuousness of the used product.

The method of discarding an absorbent article according to the invention reduces consumer anxiety related to carrying and disposing feminine care and incontinence absorbent articles by providing a more discreet way to throw away a used absorbent article, such as a menstrual pad.

While the invention has been described with reference to certain particular embodiments thereof, those skilled in the art will appreciate that various modifications may be made without departing from the spirit and scope of the invention. The scope of the invention is not to be limited to the specific embodiments described.

EXPLANATION OF NUMERALS 1 first material edge
2 second material edge
3 absorbent article
4 string end
5 string end
6 bottom of bag
7 drawstring
8 first cut out
9 second cut out
10 folded wrapper material
11 front bond
111 back bond
12 individually packaged absorbent article
13 loop
14 wrapper material bag
15 bottom axis
16 first perpendicular axis
17 second perpendicular axis
18 top front axis
19 top back axis
20 front wrapper material
21 back wrapper material
23 non-skin touching outer surface of absorbent article
24 used absorbent article
25 knot
26 used product
27 bag top
28 channel

The invention claimed is:

1. An individually packaged absorbent article, comprising:
   a wrapper material configured into an open bag configuration and comprising a drawstring, a channel, a first cut out at a loop side of the channel, and a second cut out at a string ends side of the channel, wherein the drawstring is threaded through the channel in a loop, and
   a single clean and unused absorbent article removably positioned within the wrapper material, wherein the clean and unused absorbent article is selected from the group consisting of a menstrual pad and a liner,
   wherein the first cut out and the second cut out create an inner cylinder with the drawstring near an open side of the wrapper material in the open bag configuration to secure the clean and unused absorbent article in the wrapper material, and
   wherein the wrapper material is in an initial open state.

2. The individually packaged absorbent article according to claim 1, wherein the channel is on an inside of the open bag configuration.

3. The individually packaged absorbent article according to claim 1, wherein the channel is on an outside of the open bag configuration.

4. The individually packaged absorbent article according to claim 1, wherein the drawstring comprises two string ends having a length accessible by a user.

5. The individually packaged absorbent article according to claim 1, wherein the single clean and unused absorbent article is positioned within the wrapper material in a bi-fold or a tri-fold.

6. The individually packaged absorbent article according to claim 1, wherein the single clean and unused absorbent article comprises a nonskin-touching outer surface folded over a skin-touching inner surface, and a portion of the folded nonskin-touching outer surface faces an opening of the wrapper material in the open bag configuration.

7. The individually packaged absorbent article according to claim 1, wherein the single clean and unused absorbent article absorbs at least one fluid selected from the group consisting of menstrual fluid, vagina discharge, urine, blood, and another bodily fluid.

8. The individually packaged absorbent article according to claim 1, wherein the wrapper material is at least one material selected from the group consisting of a nonwoven material, a plastic material, a plant-based material, a non-porous material, a porous material, an absorbent material, and a waterproof material.

9. The individually packaged absorbent article according to claim 1, wherein the wrapper material is a nonwoven material.

10. The individually packaged absorbent article according to claim 1, wherein the wrapper material further comprises a decorative layer.

11. The individually packaged absorbent article according to claim 1, wherein the single clean and unused absorbent article is a single-use article.

12. A hygiene kit comprising the individually packaged absorbent article according to claim 1.

13. The individually packaged absorbent article according to claim 1, wherein the clean and unused absorbent article is secured in the wrapper material by friction.

14. A method of discarding an absorbent article, comprising:

removing the single clean and unused absorbent article from the individually packaged absorbent article according to claim 1 to obtain an empty wrapper material, placing a soiled and used absorbent article into the empty wrapper material to obtain a used product, and discarding the used product.

15. The method according to claim 14, further comprising rolling, folding or otherwise condensing the soiled and used absorbent article, and knotting the drawstring.

16. A hygiene kit comprising:

at least one individually packaged absorbent article according to claim 1, and at least one hygiene product selected from the group consisting of a tampon, facial tissue, a menstrual pad, a liner, an incontinence pad, a medical pad, an overnight pad, a toothbrush, toothpaste, dental floss, a non-steroidal anti-inflammatory drug (NSAID), a cotton swab, a razor, shaving cream, shaving gel, a comb, a hairbrush, a shower cap, deodorant, antiperspirant, shampoo, conditioner, soap, a facial mask, hand lotion, body lotion, and sunscreen.

\* \* \* \* \*